US00PP36307P3

(12) United States Plant Patent
Watt

(10) Patent No.: US PP36,307 P3
(45) Date of Patent: Dec. 10, 2024

(54) ***CANNABIS* PLANT NAMED '21AF0716'**

(50) Latin Name: *Cannabis sativa*
Varietal Denomination: 21AF0716

(71) Applicant: Grace Executive Service, Inc., Oakland, CA (US)

(72) Inventor: Caitlin Watt, Oakland, CA (US)

(73) Assignee: CURALEAF DH, INC., New York, NY (US)

( * ) Notice: Subject to any disclaimer, the term of this patent is extended or adjusted under 35 U.S.C. 154(b) by 0 days.

(21) Appl. No.: 18/445,188

(22) Filed: May 16, 2023

(65) Prior Publication Data

US 2024/0008379 P1 Jan. 4, 2024

Related U.S. Application Data

(60) Provisional application No. 63/365,117, filed on May 20, 2022.

(51) Int. Cl.
*A01H 5/02* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258
See application file for complete search history.

*Primary Examiner* — Karen M Redden
(74) *Attorney, Agent, or Firm* — Hunt IP Law

(57) ABSTRACT

The unique annual herbaceous *Cannabis* plant variety '21AF0716' is provided. The variety can be distinguished by its outstanding features of increased resistance to powdery mildow, higher total yield, and larger inflorescences compared to its parents.

5 Drawing Sheets

Latin name of the genus and species:
Genus—*Cannabis.*
Species—*sativa.*
Variety denomination: The new *Cannabis* plant claimed is of the variety denominated '21AF0716'.

BACKGROUND OF THE INVENTION

Field of the Invention

The present invention relates to a new and distinct annual variety of *C. sativa*, which has been given the variety denomination of '21AF0716'. '21AF0716' is intended for use as a plant both commercially as well as for home growers, including as part of a breeding program to develop improved *Cannabis* varieties.

Background of the Related Art

The genus *Cannabis* has been in use by humans for millennia, due to the multiplicity of its benefits to humans, including the considerable value and utility of its fiber, the nutritional value of its seeds, and the medicinal value of its floral parts and products made from them. Currently the genus is under intense legal commercialization in the United States as industrial hemp for a variety of purposes including biodegradable plastics and building materials, clothing, paper, food, fuel, and medicines.

Cannabidiol (CBD) extracted from *Cannabis* is widely used in over-the-counter medicines and topical treatments and is also the active ingredient in the FDA-approved drug Epidiolex®. CBD is just one of at least dozens—perhaps hundreds—of cannabinoids endogenous to *Cannabis*, tetrahydrocannabinol (THC) being the other cannabinoid that is most well-known. The cannabinoids as a group interact with the human endocannabinoid receptors, which are distributed in the brain and throughout the body. The study of the endocannabinoid system (ECS) in humans and other mammals is an area of increasing interest and holds tremendous promise for the future of medicine. See, e.g., Russo (2019). *Cannabis* and Pain, *Pain Medicine,* 20(10): 1;20(11):2083-2085; and Russo (2016). Clinical Endocannabinoid Deficiency Reconsidered: Current Research Supports the Theory in Migraine, Fibromyalgia, Irritable Bowel, and Other Treatment-Resistant Syndromes, *Cannabis Cannabinoid Res.* 1(1): 154-165.

Non-hemp forms of *Cannabis*, frequently referred to as marijuana, have been legalized for medicinal use in many states and for recreational use (sometimes called "adult use") in a growing number of states. It is expected that the wave of legalization will continue to the point of some form of federal legalization or decriminalization.

Typically, marijuana products are available to users for purchase in specialized "dispensaries" that offer dried flower, edibles, tinctures, extracts, and the like. In some cases, a unique or unusual chemical profile, or chemotype, is attractive not only for flower sales but also for use in the preparation of extracts and/or isolates and for the manufacture of a variety of products that possess characteristics of the chemotype.

SUMMARY OF THE INVENTION

The present invention relates to a new and distinct annual variety of *C. sativa*, which has been given the variety denomination of '21AF0716'.

The new *C. sativa* variety is a selection resulting from a sexual cross of *C. sativa* plants in San Mateo County, California, in September 2021, involving a seed parent known as 'Gelato 33' (unpatented) and a pollen parent known as 'Purple Punch' (unpatented).

Selection criteria were high yield, dense flowers, and resistance to powdery mildew under greenhouse conditions.

The selection was subsequently evaluated for a number of years in California.

Asexual reproduction of the new variety by cutting propagation since 2021 in San Mateo County, California has demonstrated that the new variety reproduces true to type with all of the morphological characteristics, as herein described, firmly fixed and retained through successive generations of such asexual propagation.

Certain characteristics of the new variety have been repeatedly observed and can be used to distinguish '21AF0716' as a new and distinct variety of *C. sativa* plant. Plants of the new variety differ from plants of the seed parent 'Gelato 33' primarily in node spacing between inflorescences, increased inflorescence size, inflorescence density, yield as total weight per plant, and floral aroma. Inflorescence density relates to individual flower parts being closer together in dense flowers, leading to a firmer tactile response. Dense strains resist the pressure of hand pinching rather than breaking apart like a less dense strain. Additionally, denser strains handle machine trimming better than a less dense flower. Plants of the new variety differ from plants of the pollen parent 'Purple Punch' in increased continued growth under flowering light, increased inflorescence size, yield as total weight per plant, and floral aroma. The variety expresses increased resistance to powdery mildew, higher total yield, and larger inflorescences than either parent. It exhibits continued growth under flowering light and dark purple coloration on the inflorescences similar to the seed parent and exhibits the inflorescence density and resistance to production of stress-induced male flowers of the pollen parent. The new variety differs from its parents in that it has a higher growth rate and higher yields during winter production, with an intense purpling of flowers.

Certain characteristics of the new variety have been repeatedly observed and can be used to distinguish '21AF0716' as a new and distinct variety of *C. sativa* plant. Plants of the new variety differ from plants of the commercial variety 'Eureka' (unpatented) primarily in color. '21AF0716' contains a significant purple coloring on the plant, while 'Eureka' lacks purple coloring.

BRIEF DESCRIPTION OF THE DRAWINGS

The accompanying photographic illustrations show the typical appearance of the new variety '21AF0716'. The colors are as nearly true as is reasonably possible in a color representation of this type. Colors in the photographs may differ slightly from the color values cited in the detailed botanical description which accurately describes the colors of the new plant. Induction of flowering occurs in plants that are in vegetative growth, either by natural changes in daylength or by induction of flowering through changes in lighting of the plants. Ages provided herein are counted from the beginning of the induction of flowering and are typically reported in weeks. Because the duration of vegetative growth can be variable and can be based upon desired plant size, absolute age of plants is less relevant and can be, itself, quite variable.

DETAILED BOTANICAL DESCRIPTION

Figure 1:
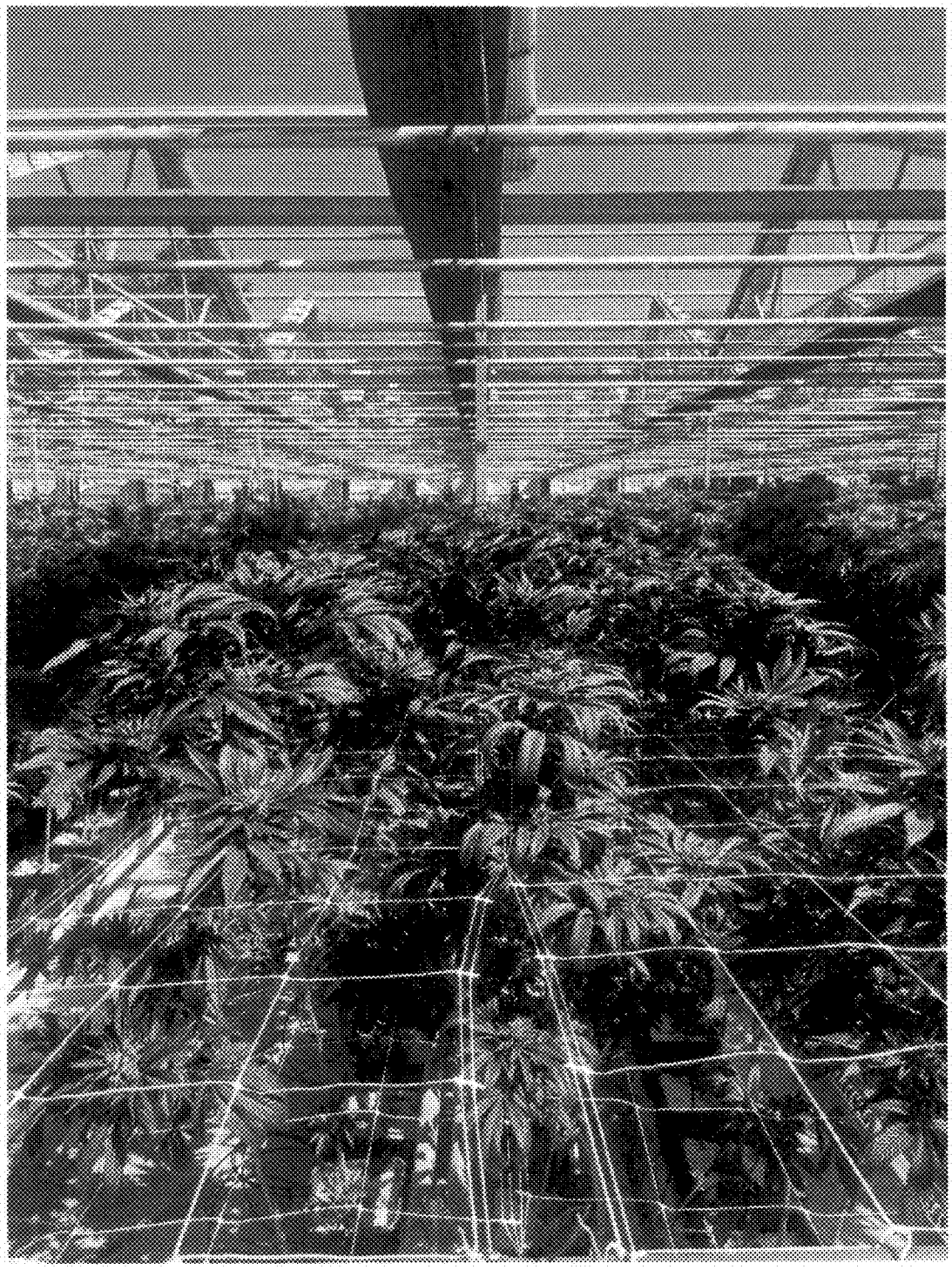
FIG. 1 is a photograph of the new variety '21AF0716', demonstrating the finished flower on a row of mature plants at 8 weeks after induction of flowering.
Figure 2:
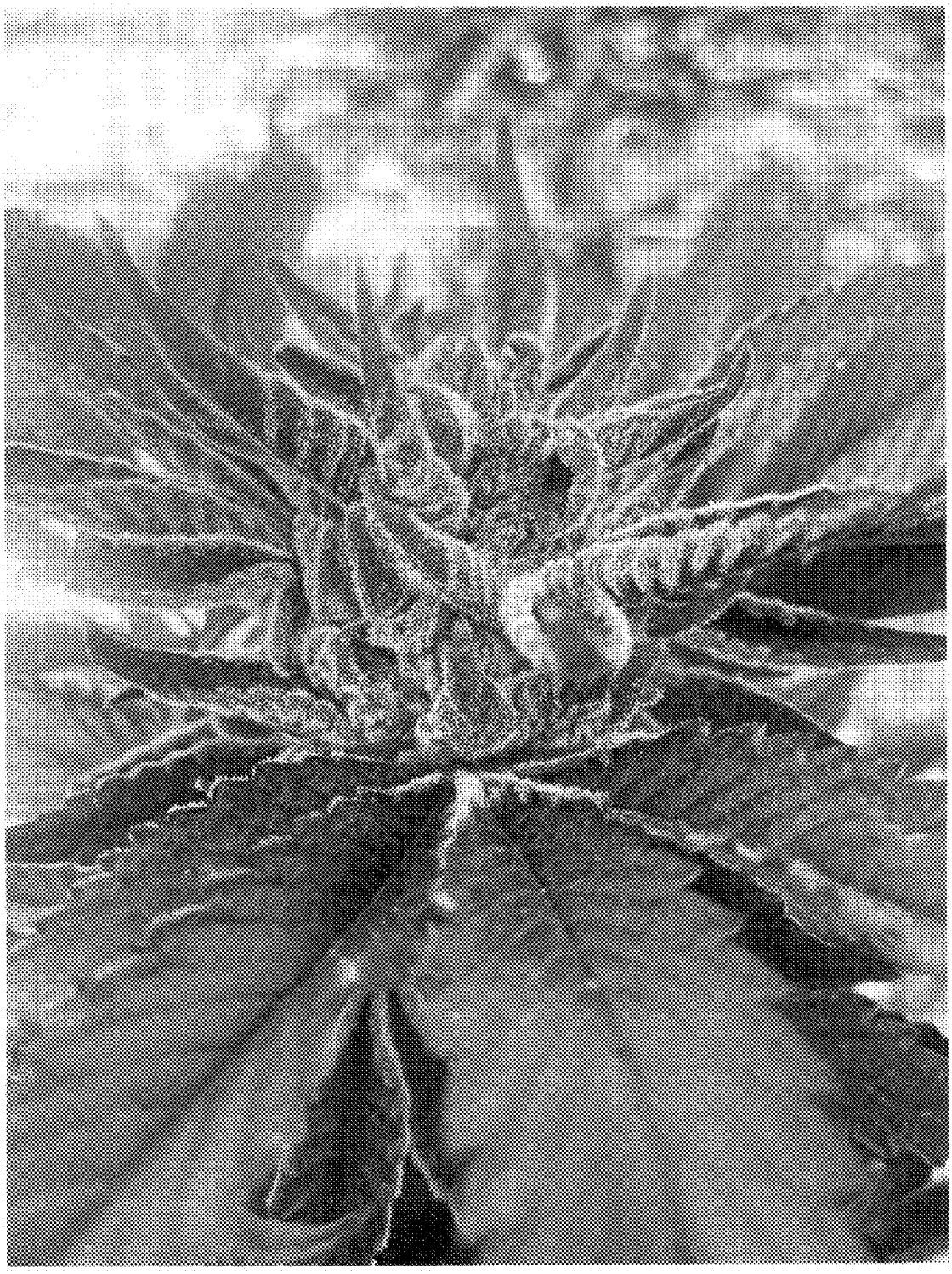
FIG. 2 is a photograph of the mature flowers of the new variety '21AF0716' at 8 weeks after induction of flowering.
Figure 3:
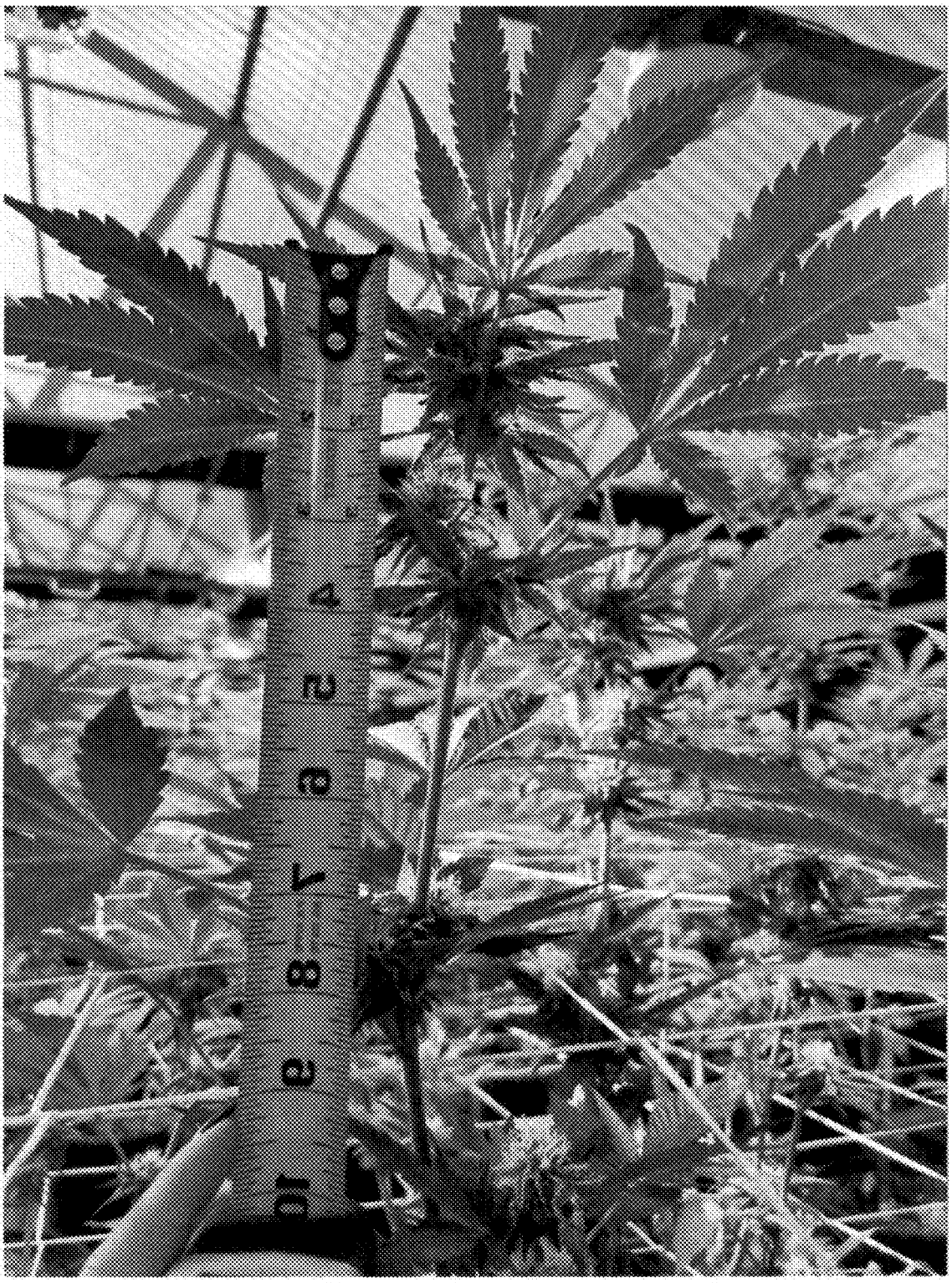
FIG. 3 is a photograph of young flowers of new variety '21AF0716' under greenhouse conditions at 3 weeks after induction of flowering.
Figure 4:
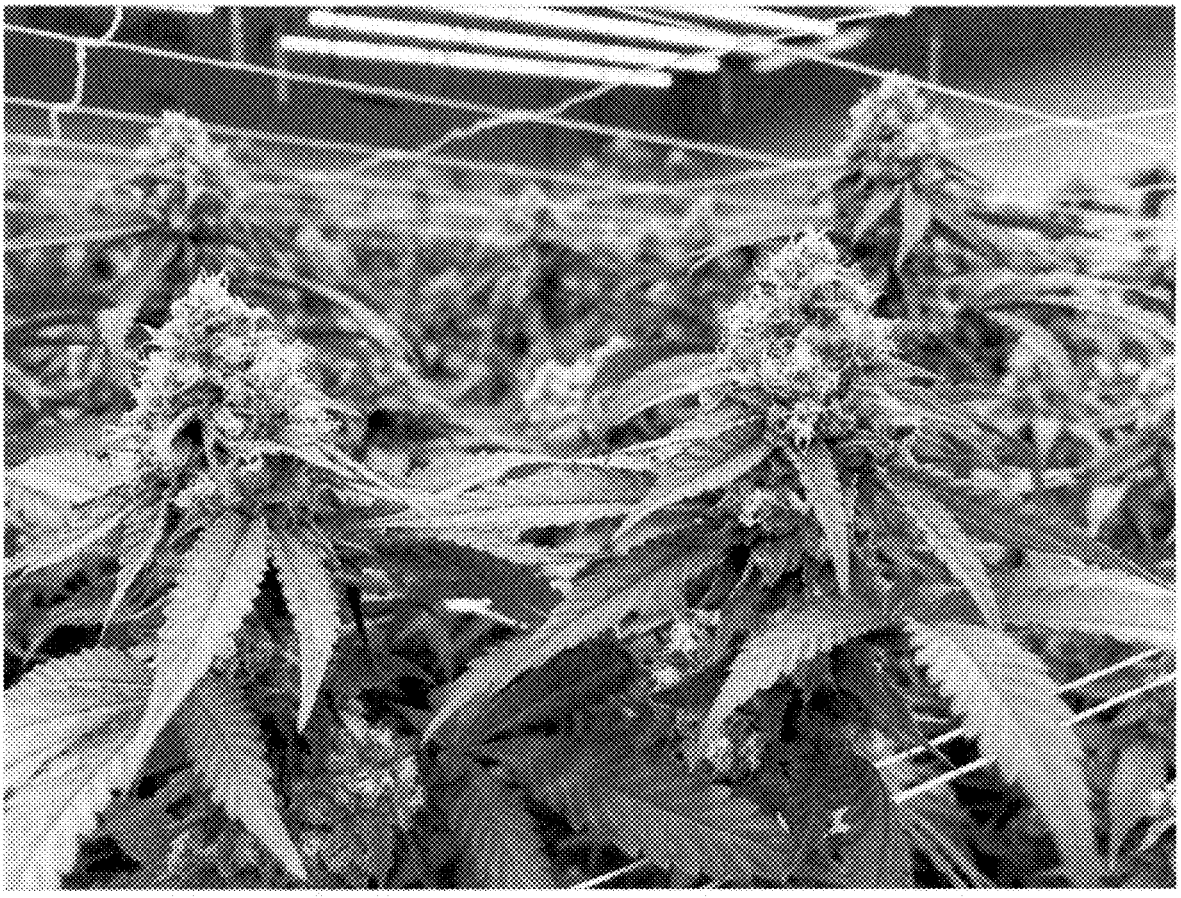
FIG. 4 is a photograph of young flowers of the new variety '21AF0716' under greenhouse conditions at 6 weeks after induction of flowering.
Figure 5:
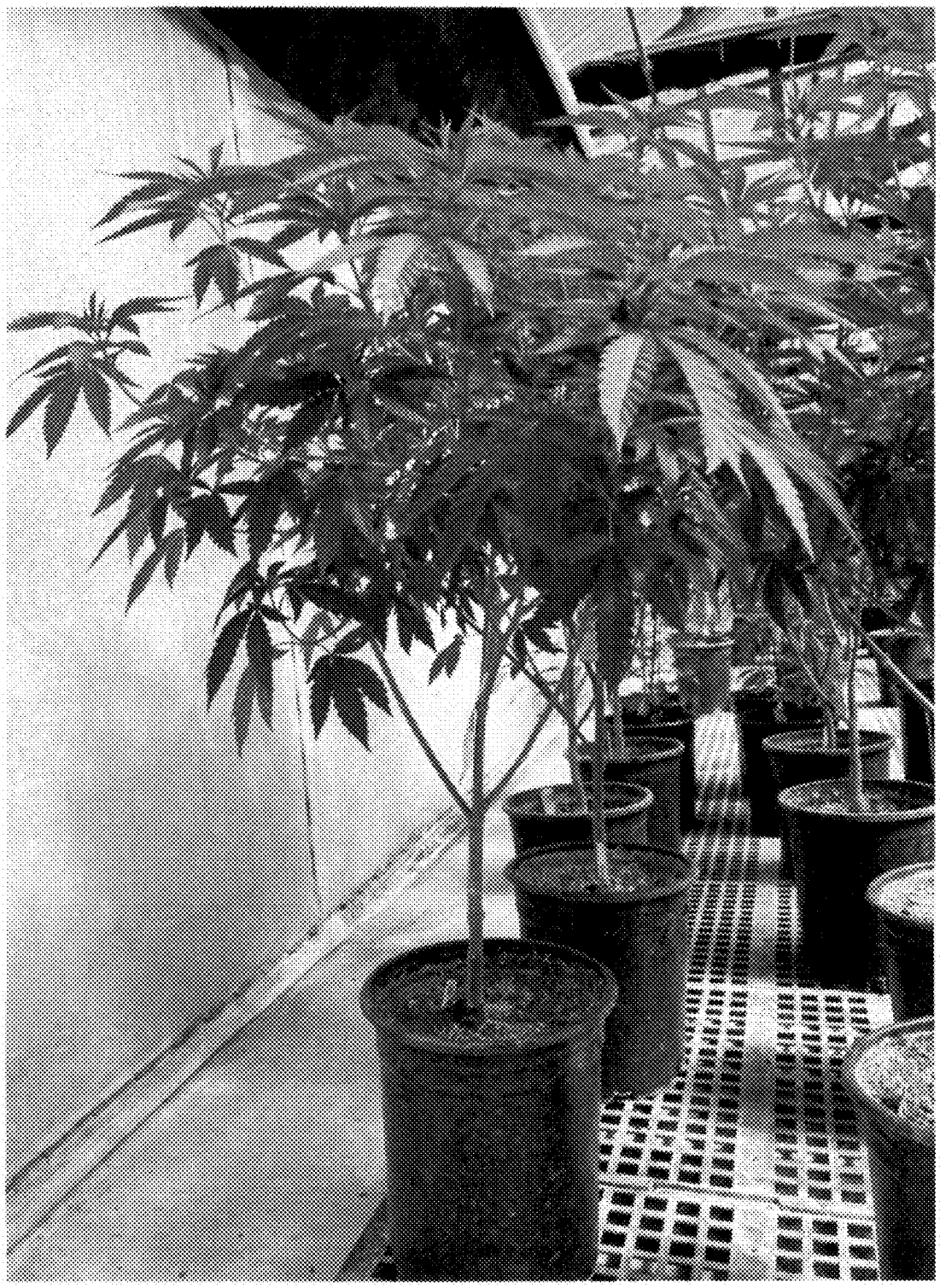
FIG. 5 is a photograph of the immature plant of the new variety '21AF0716' at 3 months of growth under vegetative conditions.

The following detailed description sets forth the distinctive characteristics of '21AF0716'. The datum which defines these characteristics was collected from asexual reproductions of the original selection. Dimensions, sizes, colors, and other characteristics are approximations and averages set forth as accurately as possible. The plant history was taken on mother plants approximately 3 months old, and the descriptions relate to plants grown in Half Moon Bay, California. Color notations are in reference to the standard hexadecimal (HEX) color code.

Type: Herbaceous annual.

Classification:

*a. Family.*—Cannabaceae.
*b. Genus.*—*Cannabis.*
*c. Species.*—*sativa.*
*d. Common name.*—Marijuana.

Parentage: 'Gelato 33' x 'Purple Punch'.

PLANT

General:

*a. Parentage.*—i. Female parent — 'Gelato 33'. ii. Reversed Female parent — 'Purple Punch'.
*b. Growth habit.*—Medium growth habit with strong branches and compact structure.
*c. Hardiness.*—USDA Zone 2 and higher.
*d. Average height.*—56 inches.
*e. Average spread.*—28 inches.
*f. Productivity.*—94 g of dry weight per 5-gallon potted plant at 3 weeks veg and 8 weeks flower time.
*g. Disease resistance/susceptibility.*—Low susceptibility to bud rot and powdery mildew under standard growing conditions. i. Powdery Mildew — *Golovinomyces ambrosiae.*
*h. Fragrance.*—Cake, cookie and gassy aroma.
*i. Proportion of hermaphrodite plants.*—Low.
*j. Proportion of female plants.*—Female plants are agronomically significant and seeds are feminized.
*k. Type of inflorescence.*—High branched compound racemose.
*l. Photoperiodicity.*—Short day photoperiod sensitive.

STEM/CENTRAL STALK

General:

*a. Average diameter of stem.*—1 inch.
*b. Average length of stem.*—48 inches.
*c. Shape.*—Tubular.
*d. Depth of grooves.*—Shallow.
*e. Pith in cross section.*—Medium.
*f. Trichome type.*—Few trichomes.

*g. Color*.—Stems are green (#49C369) with reddish/purple stripes (#a33650).

LEAF

General:

*a. Leaf arrangement*.—Alternate.
*b. Leaf shape*.—Palmately Compound.
*c. Leaf margins*.—Serrate.
*d. Leaf apex shape*.—Acuminate.
*e. Leaf base shape*.—Attenuate.
*f. Number of leaflets per leaf*.—5-7.
*g. Trichome type* (*top surface*).—On sugar leaves near inflorescences numerous cystolithic hair, bulbous, capitate sessile or capitate stalked.
*h. Texture of top and bottom surfaces*.—Pubescent leaves.
*i. Venation type*.—Pinate.
*j. Length*.—6 in.
*k. Width*.—1.5 in.
*l. Color of upper surface*.—Dark green #007848.
*m. Color of lower surface*.—Bright green #74C365.

PETIOLE

General:

*a. Surface texture*.—Pubescent.
*b. Anthocyanin intensity*.—Intense at end of growing season.
*c. Color*.—Stems are green (#49C369) with reddish/purple stripes (#a33650).
*d. Length*.—⅛ of an inch at 3 weeks of vegetation and having been topped.
*e. Diameter*.—5-15 mm.

INFLORESCENCE

General:

*a. Natural flowering season*.—Summer.
*b. Color*.—Purple (#A020F0). i. Trichome type — Numerous cystolithic hair, bulbous, capitate sessile or capitate stalked, trichomes start clear turning to amber over time.
*c. Stigma color*.—White (##FFFAF0).
*d. Bract color*.—#32CD32, turns purple at the latter part of flowering stage.
*e. Shape*.—Oval. Flower spirals around the stalks.
*f. Length*.—75 mm.
*g. Width*.—38 mm.
*h. Internodal spacing*—78.2 mm.

'21AF0716' can include a cannabinoid profile as set forth in Table 1. Chemotypic characteristics of the new variety are variable based upon cultivation conditions, as is typical of *Cannabis* plants. Accordingly, while chemotypic information provided herein is representative of performance of the new varieties under a particular set of cultivation conditions, it is not limiting on other chemotypic profiles obtainable under a different set of cultivation conditions. Thus, the values set forth in Table 1 do not reflect the only possible range of outcomes that can be obtained from plants of the new variety. These values are merely exemplary of observed values (middle column) and predicted normal variations from the observed values.

TABLE 1

Exemplary Profiles of Key Cannabinoids.

| Cannabinoid | Percent | Percent | Percent | Percent | Percent |
|---|---|---|---|---|---|
| THCa | 17.63625 | 18.812 | 23.515 | 28.218 | 29.39375 |
| Delta 9 THC | 0.472425 | 0.50392 | 0.6299 | 0.75588 | 0.787375 |
| CBGa | 0.4206 | 0.44864 | 0.5608 | 0.67296 | 0.701 |
| CBCa | 0.141375 | 0.1508 | 0.1885 | 0.2262 | 0.235625 |
| THCVa | 0.054075 | 0.05768 | 0.0721 | 0.08652 | 0.090125 |
| CBDa | 0.03255 | 0.03472 | 0.0434 | 0.05208 | 0.05425 |
| CBG | 0.031725 | 0.03384 | 0.0423 | 0.05076 | 0.052875 |
| Total THC | 15.939375 | 17.002 | 21.2525 | 25.503 | 26.56563 |
| Total CBD | 0.028575 | 0.03048 | 0.0381 | 0.04572 | 0.047625 |
| Total Cannabinoid | 11.0266 | 17.64256 | 22.0532 | 26.46384 | 27.5665 |

* Total THC = (THCA * 0.877) + THC (i.e., delta 9 THC) + delta 8 THC
** Total CBD = CBD + (CBDa * 0.877)
*** Total Cannabinoids = Total THC + Total CBD +Total CBG + Total THCV + Total CBC +Total CBDV + Δ8THC + CBL + CBN]

What is claimed is:

1. A new and distinct variety of *Cannabis* plant named '21AF0716', as illustrated and described herein.

* * * * *